(12) United States Patent
Keeley et al.

(10) Patent No.: US 12,394,509 B2
(45) Date of Patent: *Aug. 19, 2025

(54) ARTIFICIALLY INTELLIGENT REMOTE PHYSICAL THERAPY AND ASSESSMENT OF PATIENTS

(71) Applicant: Electronic Caregiver, Inc., Las Cruces, NM (US)

(72) Inventors: David W. Keeley, Frisco, TX (US); Anthony Dohrmann, El Paso, TX (US); Robert Wood, Las Cruces, NM (US)

(73) Assignee: Electronic Caregiver, Inc., Las Cruces, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/737,757

(22) Filed: Jun. 7, 2024

(65) Prior Publication Data

US 2024/0412844 A1 Dec. 12, 2024

Related U.S. Application Data

(63) Continuation of application No. 17/526,839, filed on Nov. 15, 2021, now Pat. No. 12,009,083.

(60) Provisional application No. 63/114,045, filed on Nov. 16, 2020.

(51) Int. Cl.
| | |
|---|---|
| *G16H 20/30* | (2018.01) |
| *A61B 5/00* | (2006.01) |
| *G06F 3/048* | (2013.01) |
| *G06N 20/00* | (2019.01) |
| *G16H 10/60* | (2018.01) |

(Continued)

(52) U.S. Cl.
CPC ............ *G16H 20/30* (2018.01); *A61B 5/744* (2013.01); *G06F 3/048* (2013.01); *G06N 20/00* (2019.01); *G16H 10/60* (2018.01); *G16H 30/00* (2018.01); *G16H 40/67* (2018.01)

(58) Field of Classification Search
CPC .... G08B 21/182; G08B 3/1016; G08B 25/10; H01M 4/32; H01M 6/32; H01M 2004/027; H01M 10/425; H04W 4/38; B65D 51/24
USPC .................................................. 340/539.11
See application file for complete search history.

(56) References Cited

U.S. PATENT DOCUMENTS

| | | | |
|---|---|---|---|
| 2018/0082553 A1* | 3/2018 | Difalco | G08B 13/1436 |
| 2019/0034999 A1* | 1/2019 | Sant | G06Q 30/0633 |
| 2019/0156398 A1* | 5/2019 | Sant | G01G 15/006 |

* cited by examiner

*Primary Examiner* — Omar Casillashernandez
(74) *Attorney, Agent, or Firm* — Carr & Ferrell LLP

(57) ABSTRACT

Systems and methods for physical therapy and training delivery are presented herein. These technologies may comprise notifying a patient of a scheduled prescribed activity via an on-location at least one client device or console; identifying the patient with one or more sensors connected to or part of the at least one client device or console; confirming, via the at least one client device or console, the patient's acknowledgment of the notification; demonstrating, via a graphical interactive avatar displayed on the at least one client device or console, the prescribed activity to be carried out by the patient; confirming, via the at least one client device or console, that the patient is undertaking or will be undertaking the prescribed activity; capturing, via the one or more sensors, frames of the patient undertaking the prescribed activity; and processing frames of the patient undertaking the prescribed activity.

20 Claims, 18 Drawing Sheets

(51) Int. Cl.
*G16H 30/00* (2018.01)
*G16H 40/67* (2018.01)

| Run Test | Date | User | FPS | Number of Reps | Cu Predicted Reps | Wr Pre |
|---|---|---|---|---|---|---|
| | 2:56:55 PM Wed 21 Oct 2020 | Danny | 27 | 5 | 3 | |
| | 2:47:13 PM Wed 21 Oct 2020 | Danny | 27 | 5 | 5 | |
| | 2:45:11 PM Wed 21 Oct 2020 | Danny | 27 | 5 | 5 | |
| | 2:43:59 PM Wed 21 Oct 2020 | Danny | 27 | 5 | 5 | |
| | 2:42:33 PM Wed 21 Oct 2020 | Danny | 27 | 5 | 5 | |
| | 1:56:52 PM Wed 21 Oct 2020 | David | 27 | 5 | 5 | |
| | 1:55:32 PM Wed 21 Oct 2020 | David | 27 | 5 | 5 | |
| | 1:52:57 PM Wed 21 Oct 2020 | Kendall | 27 | 5 | 5 | |
| | 1:51:43 PM Wed 21 Oct 2020 | Kendall | 27 | 5 | 5 | |
| | 1:50:27 PM Wed 21 Oct 2020 | Abby | 27 | 5 | 5 | |
| | 1:46:56 PM Wed 21 Oct 2020 | Abby | 27 | 5 | 5 | |
| | 1:45:51 PM Wed 21 Oct 2020 | Abby | 27 | 5 | 5 | |
| | 1:40:29 PM Wed 21 Oct 2020 | Maddy | 27 | 5 | 5 | |
| | 1:39:25 PM Wed 21 Oct 2020 | Maddy | 27 | 5 | 5 | |
| | 1:36:54 PM Wed 21 Oct 2020 | Maddy | 27 | 5 | 5 | | addison care

- User Guide
- Run Motion Analysis
- Results History
- Edit Wrnch Key

Select a Test Type: Numbered STS

Cu Predicted Velocity    Key Points

TO FIG. 7B

FIG. 7A ered STS Results Data

| dicted Reps | Cu Residual | Wr Residual | Cu Predicted Velocity | Wr Predicted Velocity | Stopwatch Time | Cu Time | Wr Time | Stopwatch Velocity |
|---|---|---|---|---|---|---|---|---|
| 3 | 0.123 | 0.09 | 12.987 | 12.955 | 21.454 | 13.861 | 13.894 | 13.983 |
| 5 | -0.114 | -0.181 | 18.007 | 18.131 | 18.131 | 16.66 | 16.727 | 16.546 |
| 5 | -0.073 | -0.006 | 18.205 | 18.286 | 18.286 | 16.479 | 16.412 | 16.406 |
| 5 | -0.384 | -0.184 | 23.662 | 24.401 | 24.401 | 12.678 | 12.478 | 12.295 |
| 5 | 0.042 | 0.042 | 18.655 | 18.655 | 18.606 | 16.082 | 16.082 | 16.124 |
| 5 | -0.066 | -0.2 | 21.06 | 20.864 | 21.158 | 14.245 | 14.379 | 14.179 |
| 5 | 0.02 | -0.114 | 19.807 | 19.577 | 19.781 | 15.146 | 15.28 | 15.166 |
| 5 | -0.046 | 0.021 | 18.501 | 18.577 | 18.553 | 16.216 | 16.149 | 16.17 |
| 5 | -0.009 | -0.076 | 17.911 | 17.84 | 17.921 | 16.75 | 16.816 | 16.741 |
| 5 | -0.301 | -0.268 | 22.993 | 23.052 | 23.537 | 13.047 | 13.014 | 12.746 |
| 5 | -0.372 | -0.072 | 24.837 | 25.47 | 25.626 | 12.079 | 11.779 | 11.707 |
| 5 | -0.378 | -0.244 | 14.965 | 15.066 | 15.253 | 20.046 | 19.913 | 19.669 |
| 5 | -0.332 | -0.132 | 19.813 | 20.078 | 20.257 | 15.141 | 14.942 | 14.81 |
| 5 | -0.011 | 0.056 | 14.121 | 14.165 | 14.128 | 21.245 | 21.178 | 21.234 |
| 5 | -0.292 | 0.042 | 20.21 | 20.674 | 20.615 | 14.844 | 14.511 | 14.552 | st Totals (All Results)

| Average | Minimum | Maximum |
|---|---|---|
| 22.079 | 0.000 | 77.081 |

← 700

FROM FIG. 7A

FIG. 7B

ARTIFICIALLY INTELLIGENT REMOTE PHYSICAL THERAPY AND ASSESSMENT OF PATIENTS

CROSS-REFERENCE TO RELATED APPLICATIONS

The present continuation application claims the priority benefit of U.S. Non-Provisional patent application Ser. No. 17/526,839, filed on Nov. 15, 2021, titled "Remote Physical Therapy and Assessment of Patients," which claims the priority benefit of U.S. Provisional Patent Application No. 63/114,045, filed on Nov. 16, 2020, and titled "Methods and Systems for Remote Physical Therapy and Assessment of Patients", which is hereby incorporated by reference in its entirety.

The present application is related to U.S. patent Ser. No. 10/813,572, issued on Oct. 27, 2020, and titled "Intelligent System for Multi-Function Electronic Caregiving to Facilitate Advanced Health Monitoring, Fall and Injury Prediction, Health Maintenance and Support, and Emergency Response", which is hereby incorporated by reference in its entirety.

FIELD OF INVENTION

The present technology pertains to remote physical therapy. In particular, but not by way of limitation, the present technology provides systems and methods of remote physical therapy and assessment of patients.

SUMMARY

In various embodiments, the present disclosure is directed to methods carried out on a system and executed on one or more computing devices, which can be configured to perform particular operations or actions by virtue of having software, firmware, hardware, or a combination thereof installed on the system and/or computing devices that in operation causes or cause the system to perform actions and/or method steps to enable remote physical therapy.

In some embodiments the present technology is directed to a system for remote physical therapy and assessment of patients, the system comprising: a) an at least one on-location sensor to capture and transmit visual data; b) an at least one on-location client device to display personalized instructions; c) an interactive graphical user interface to display the personalized instructions on the at least one on-location client device; d) a server system that includes: an AI virtual game engine (also referred to herein as "AI", "AI game engine", or "AI engine"), to analyze the visual data and produce updated personalized instructions; an at least one processor; a memory communicatively coupled to the at least one processor, the memory storing instructions executable by the processor to run the AI virtual game engine; and e) a network; whereby the network is connected to the server system, the at least one on-location sensor and the at least one on-location client device. The on-location sensor may be a depth of field camera. The remote physical therapy system may include, connect to and/or integrate with electronic medical record system(s). The AI virtual game engine may also use data from the electronic medical record system to produce updated personalized instructions, routines, movements, or physical therapy plans, separately or in addition to data the system collects itself. The network in this system may also be a content delivery network. The network may also connect to additional or fewer devices and systems.

Embodiments of the present technology may also be directed to systems and methods for physical therapy training and delivery (referred to herein as "PTTD"). PTTD is an artificial intelligence virtual physical therapy exergame application that remotely delivers clinically prescribed fitness regimens through a graphical user interface (GUI) with instructional animation by a virtual caregiver avatar. PTTD integrates artificial intelligence into its motion analysis software that allows a user/patient to measure their physical progress. The application may be used to supplement home fitness programs that are prescribed by the user's clinician(s) for preventive and rehabilitative physical therapy or by the user's physical trainers for sports cross-training. Clinicians and fitness/sports organizations may register for PTTD. This allows clinicians to remotely promote their care plan to the patient who is in the home and provides further insight into patient outcome progress. PTTD does this by integrating machine learning algorithms (MLA) into joint tracking motion analysis for user-compliance detection and kinesthetic progress. Moreover, PTTD includes clinically validated exercise animations, and allows for user or third-party access to joint-tracking data for external validation of users' regimens.

BRIEF DESCRIPTION OF THE DRAWINGS

In the description, for purposes of explanation and not limitation, specific details are set forth, such as particular embodiments, procedures, techniques, etc. to provide a thorough understanding of the present technology. However, it will be apparent to one skilled in the art that the present technology may be practiced in other embodiments that depart from these specific details.

The accompanying drawings, where like reference numerals refer to identical or functionally similar elements throughout the separate views, together with the detailed description below, are incorporated in and form part of the specification, and serve to further illustrate embodiments of concepts that include the claimed disclosure and explain various principles and advantages of those embodiments.

Figure 1:
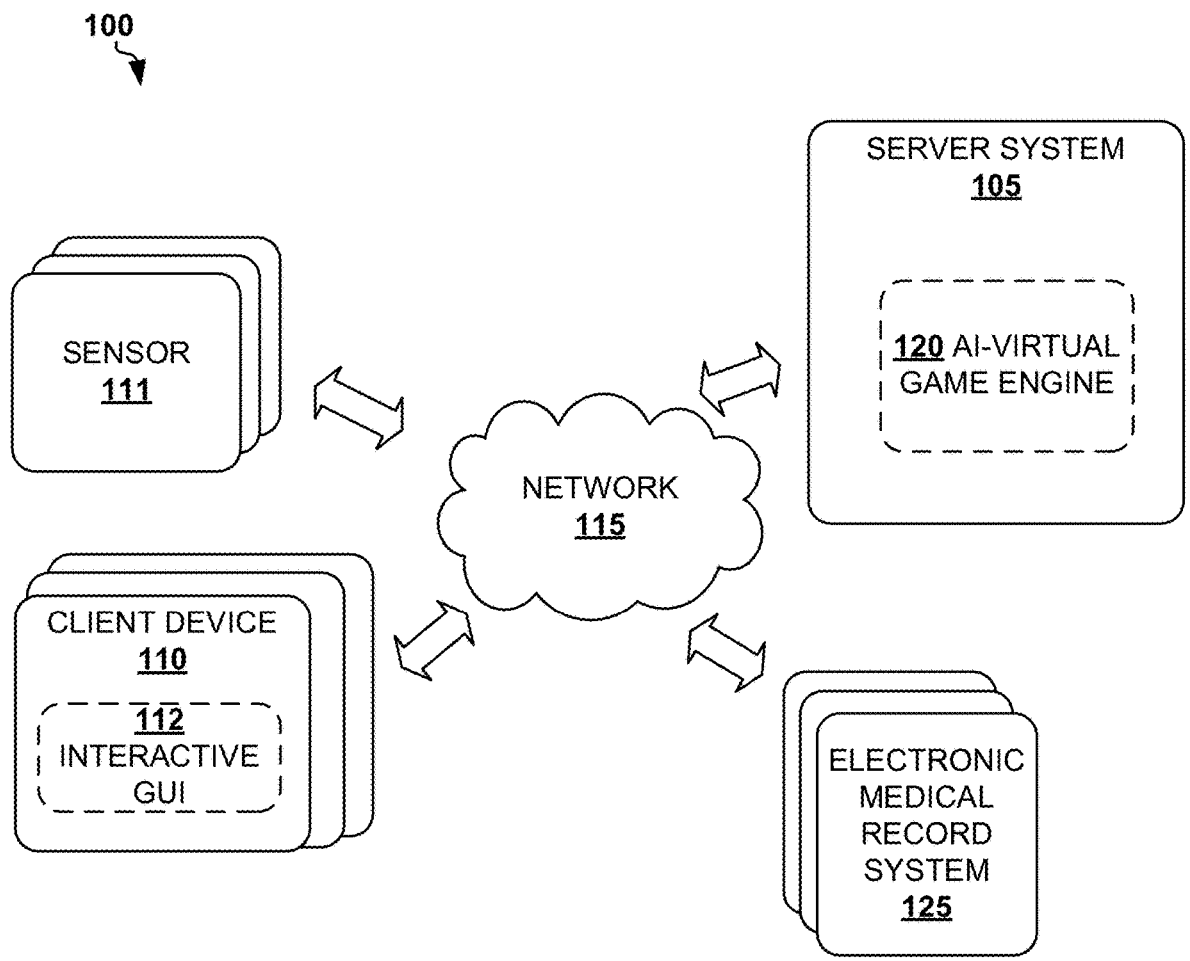

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIG. 1 presents a schematic diagram of an exemplary system for remote physical therapy.

Figure 2:
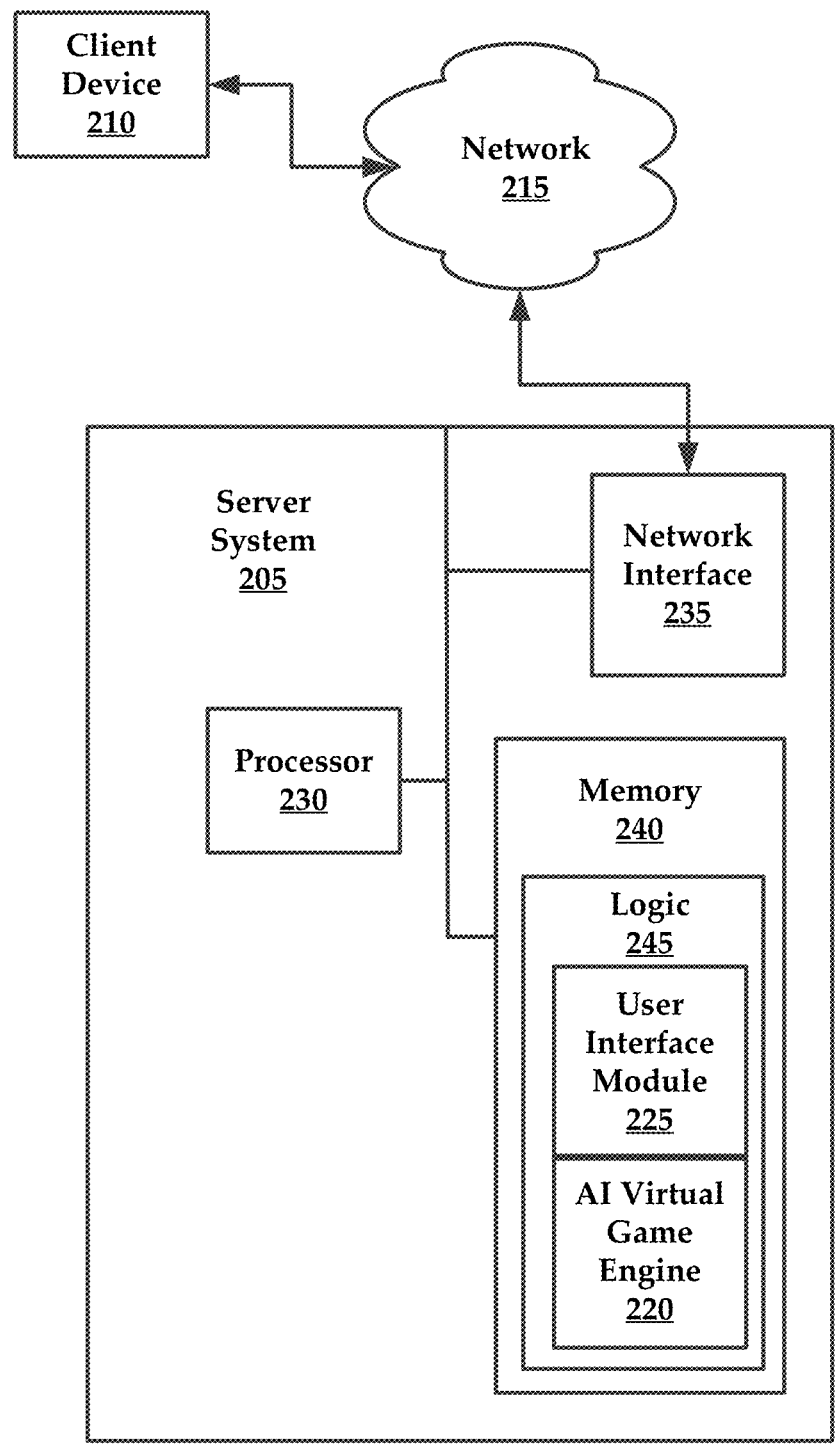

FIG. 2 presents a schematic diagram of an exemplary computing architecture that can be used to practice aspects of the present technology.

Figure 3:
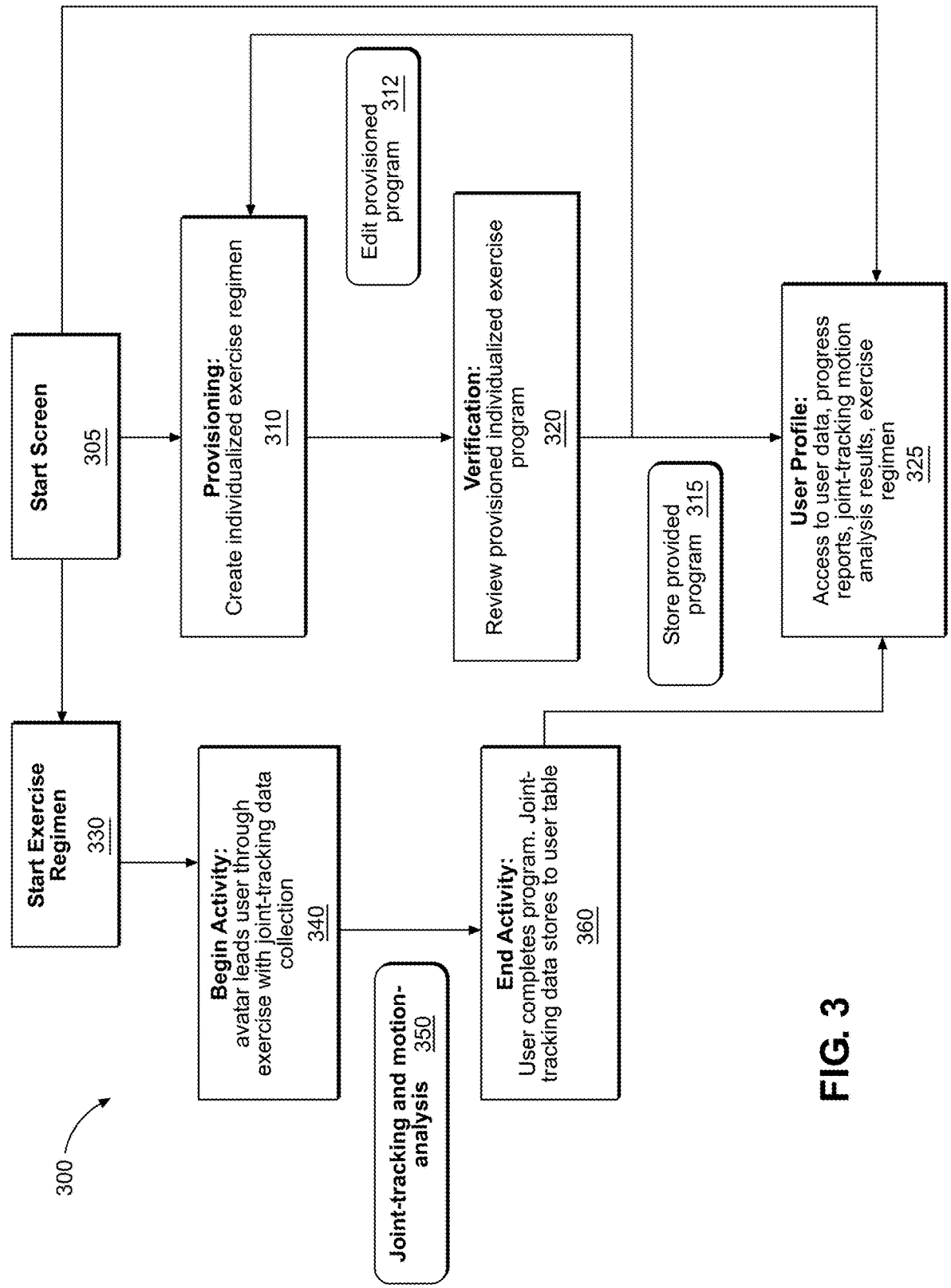

FIG. 3 presents the basic flow of one embodiment of a user profile set.

Figure 4:
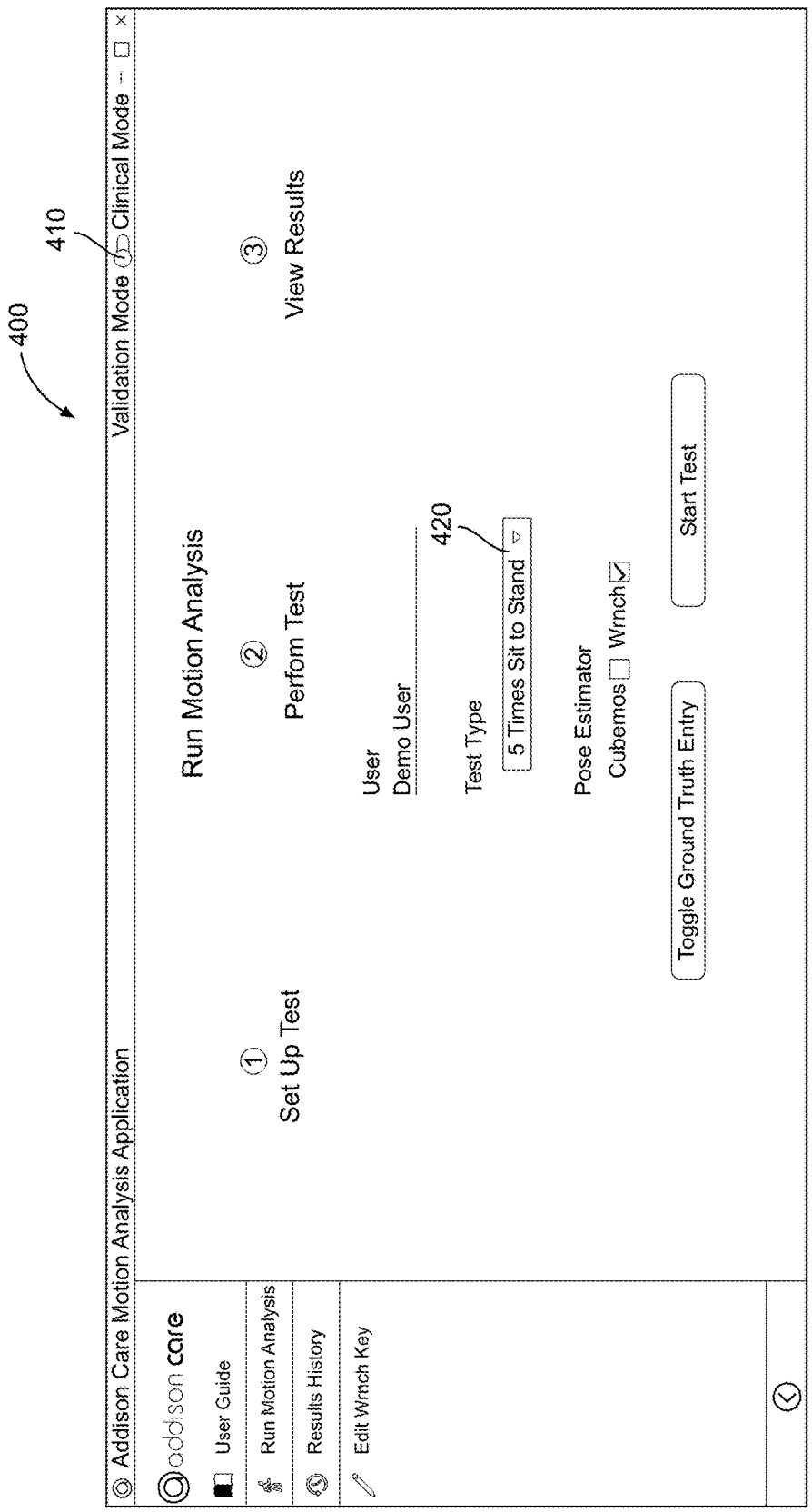

FIG. 4 presents one embodiment the initial interface to run motion analysis assessment in either clinical or validation modes.

Figure 5:
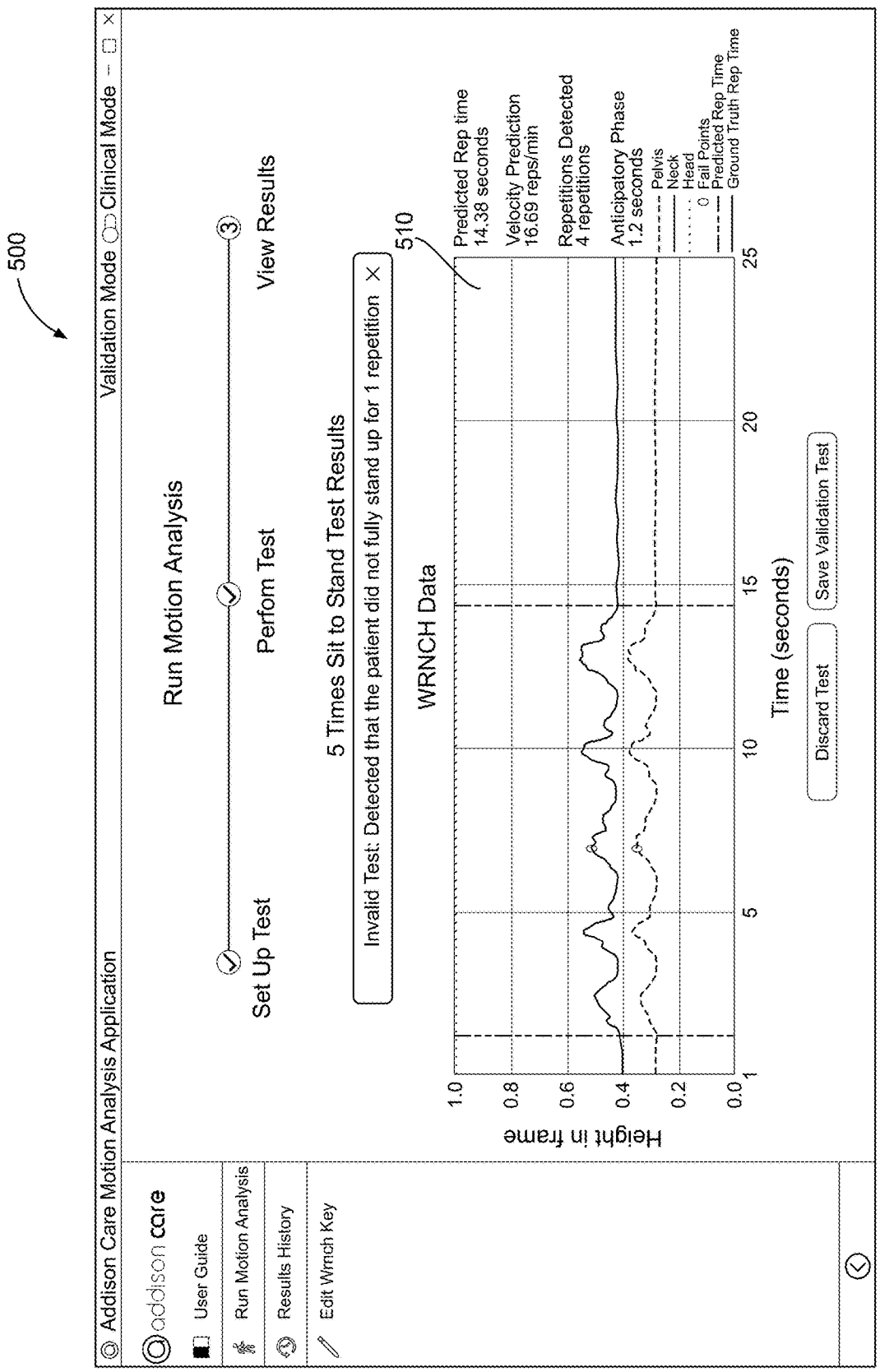

FIG. 5. presents one embodiment of the motion analysis joint-tracking interface.

Figure 6:
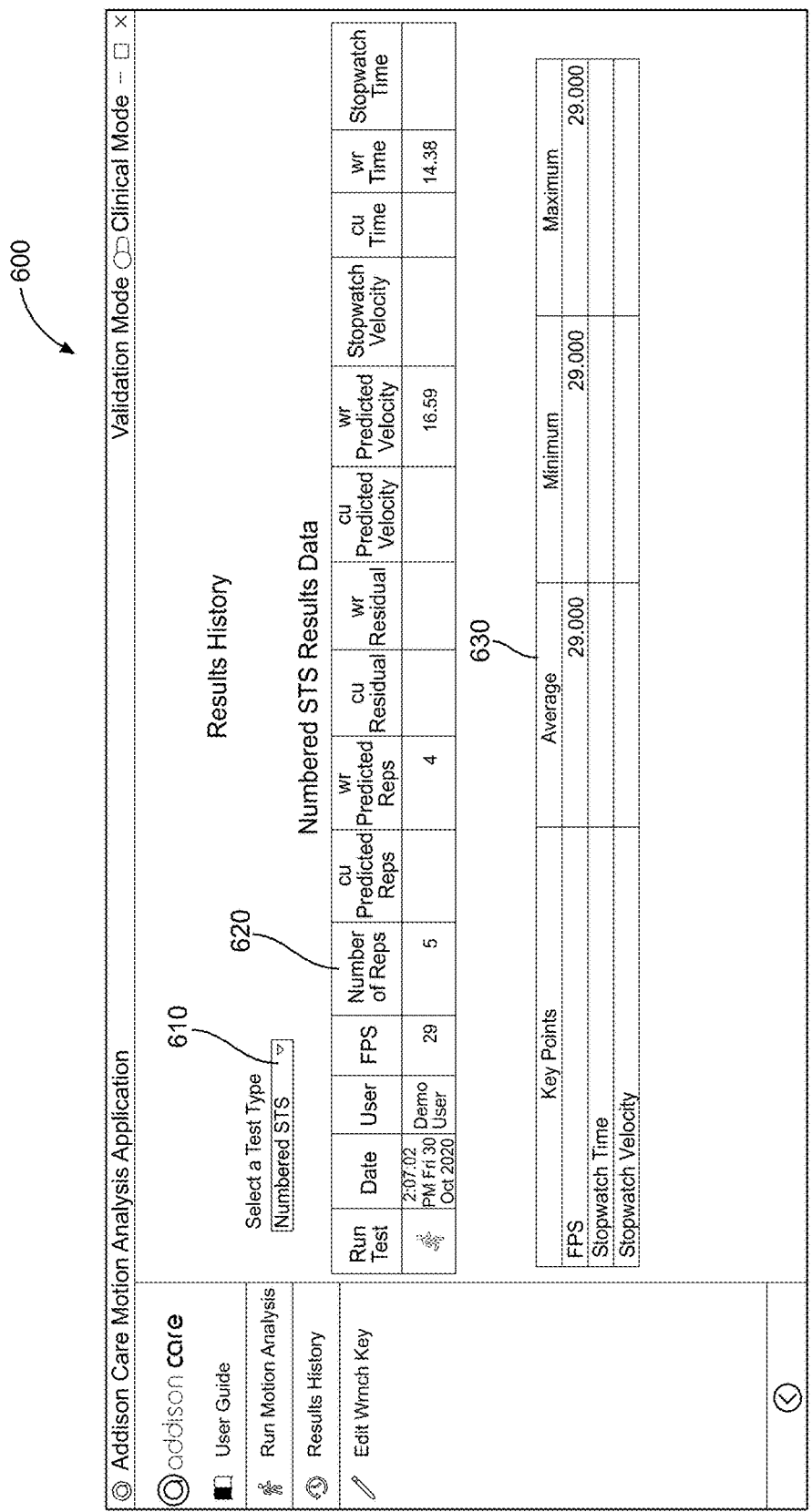

FIG. 6. presents an embodiment of an interface that allows clinicians to review multiple users' results.

FIGS. 7A-7D illustrate one embodiment of an interface for multi-user ground truth comparison.

Figure 8:
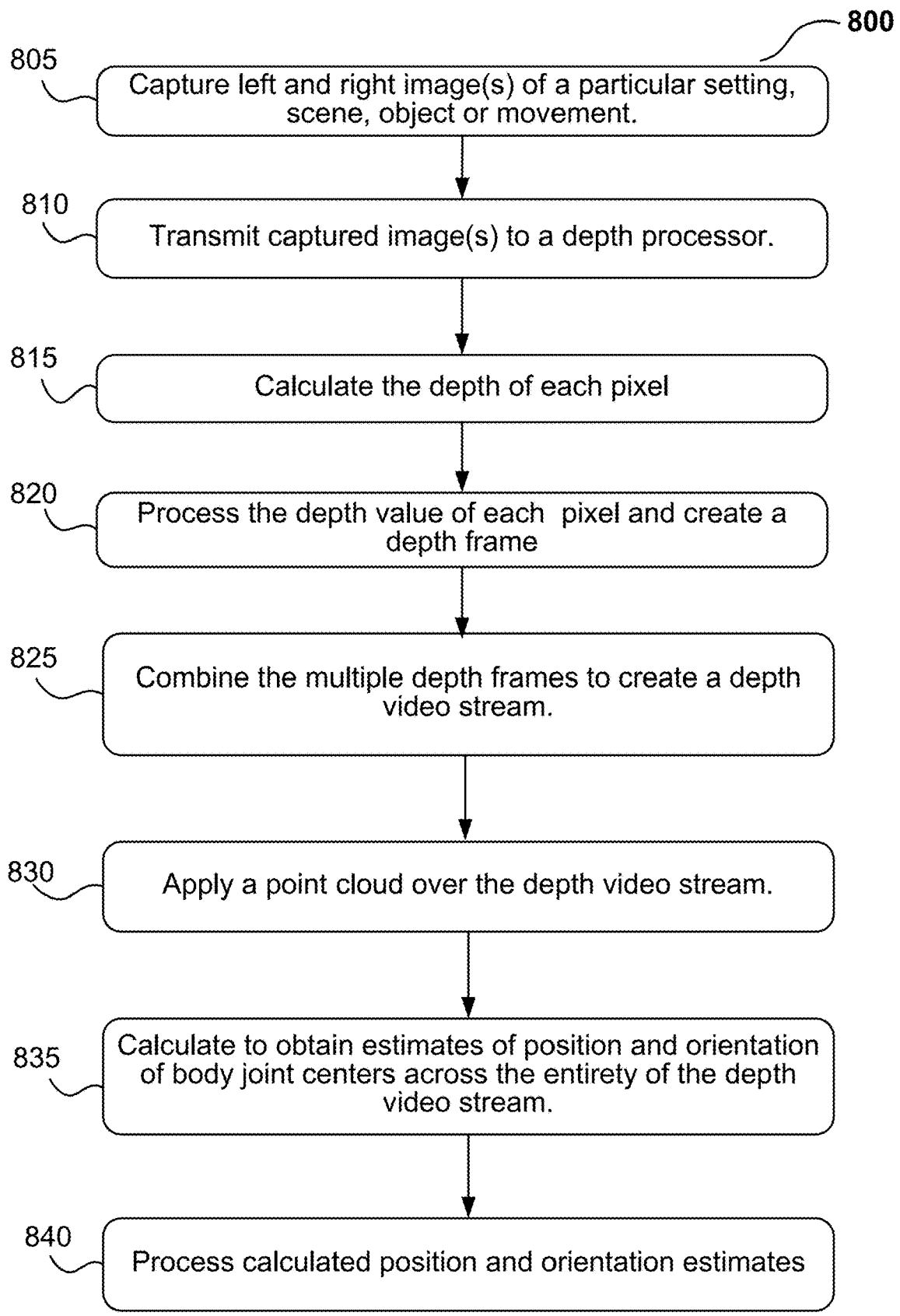

FIG. 8 presents a flow diagram of a method to process depth image and scene data as part of the PTTD system.

Figure 9A:
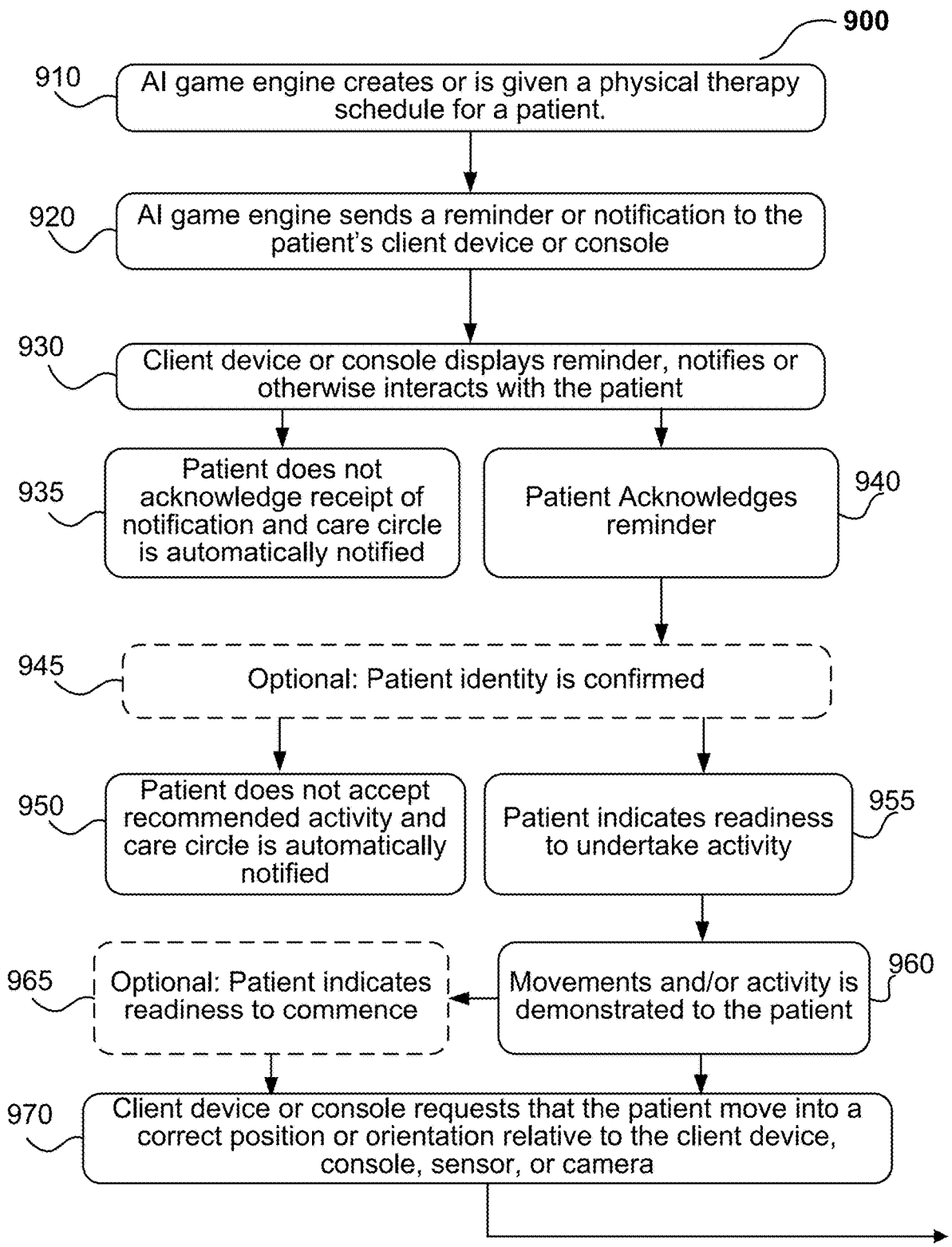
Figure 9B:
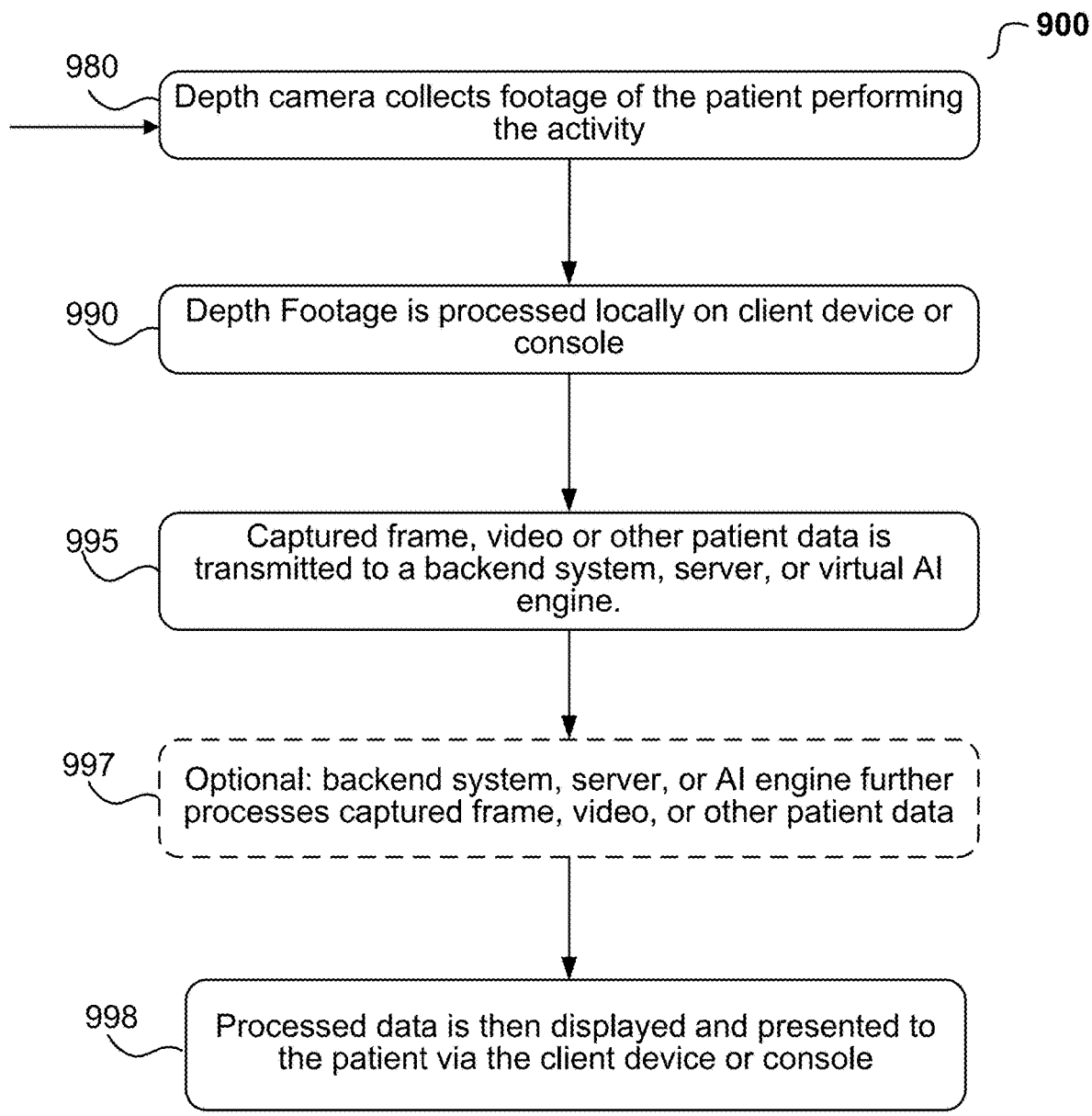

FIGS. 9A and 9B present a diagram for a method for physical therapy and training delivered by an exemplary AI game engine.

Figure 10A:
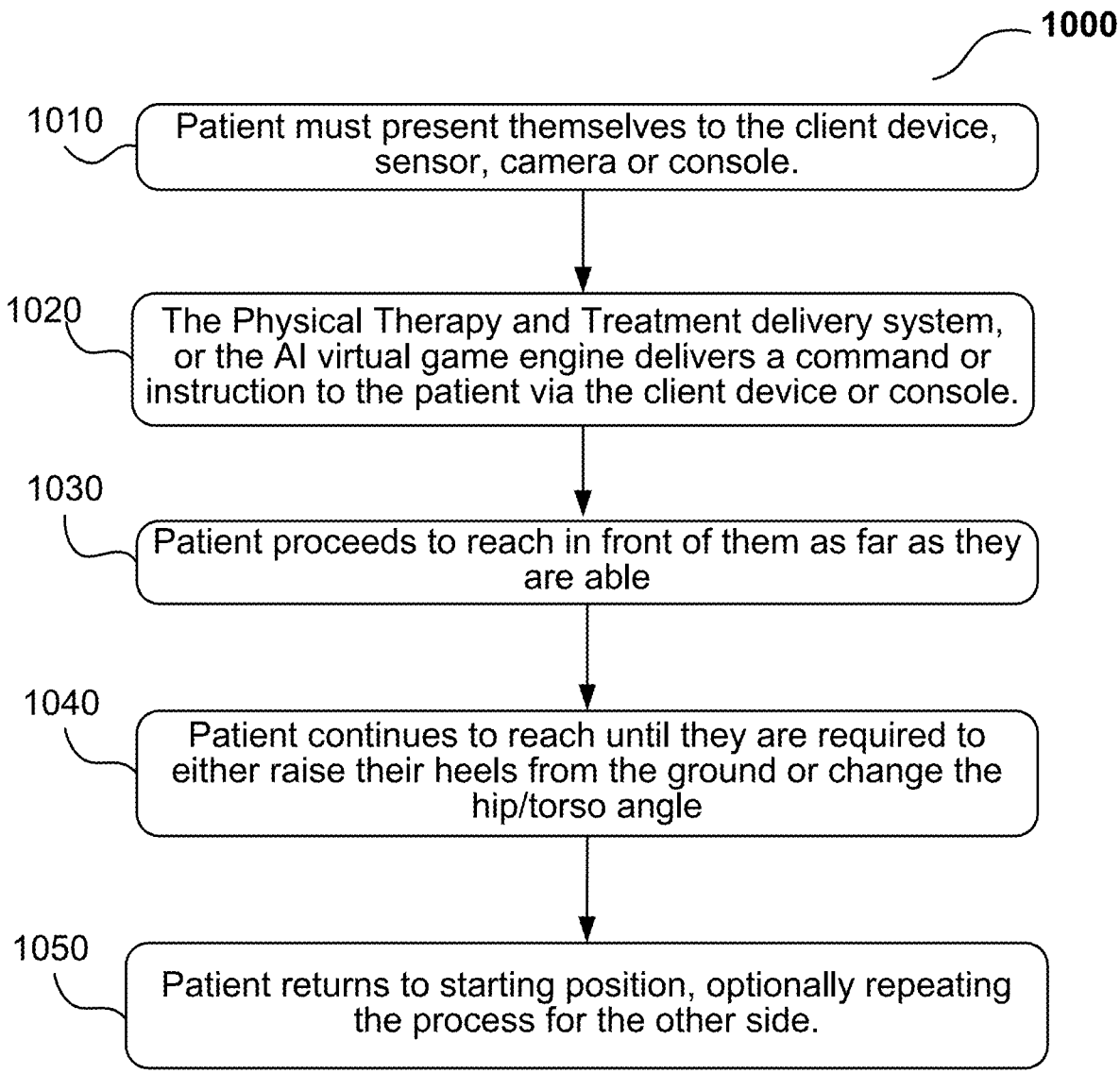

FIG. 10A presents one possible embodiment of a functional reach testing protocol carried out by the PTTD system for patients.

Figure 10B:
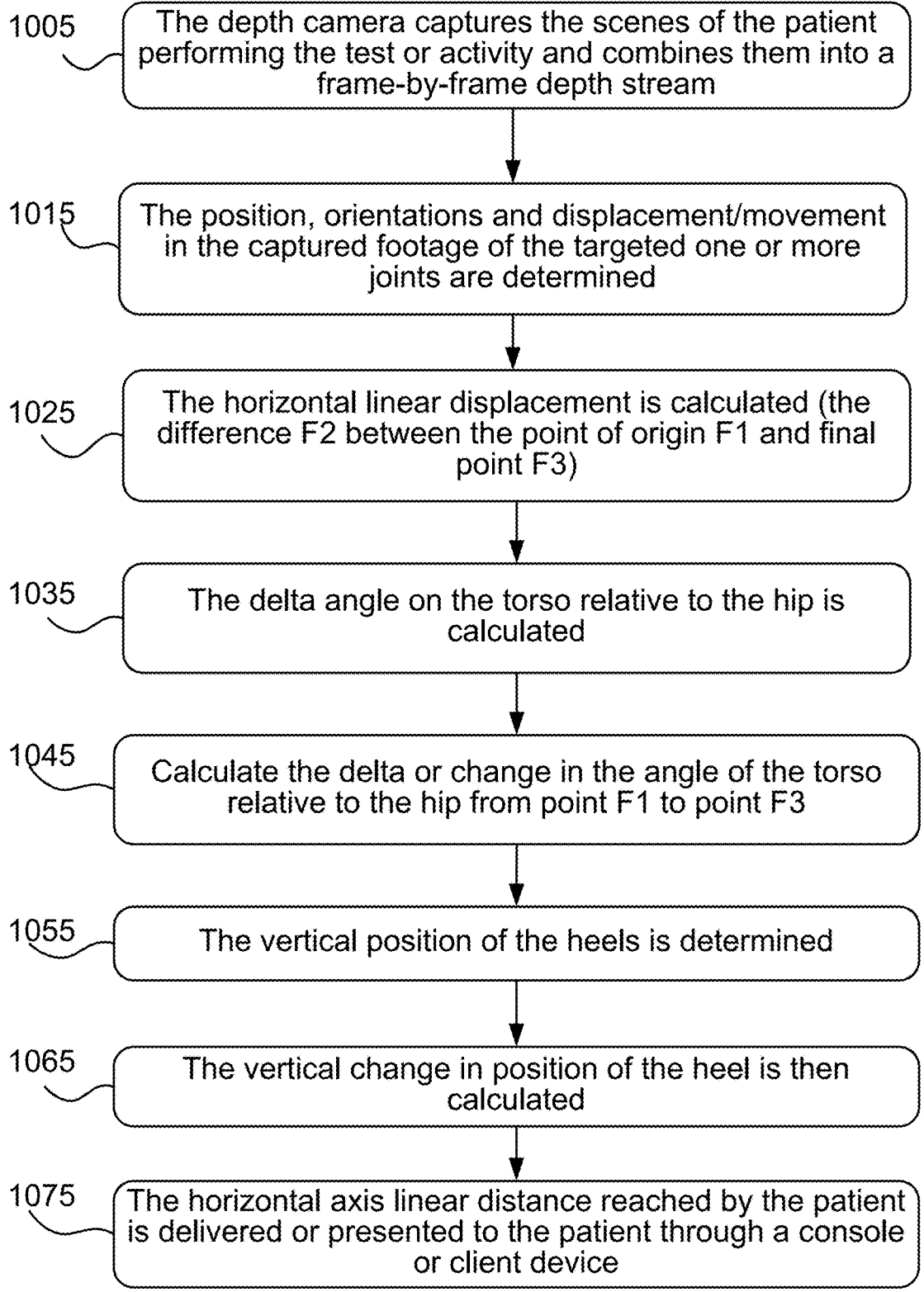

FIG. 10B presents one possible embodiment of the calculations carried out by the PTTD system and/or the AI game engine for a functional reach test.

Figure 11A:
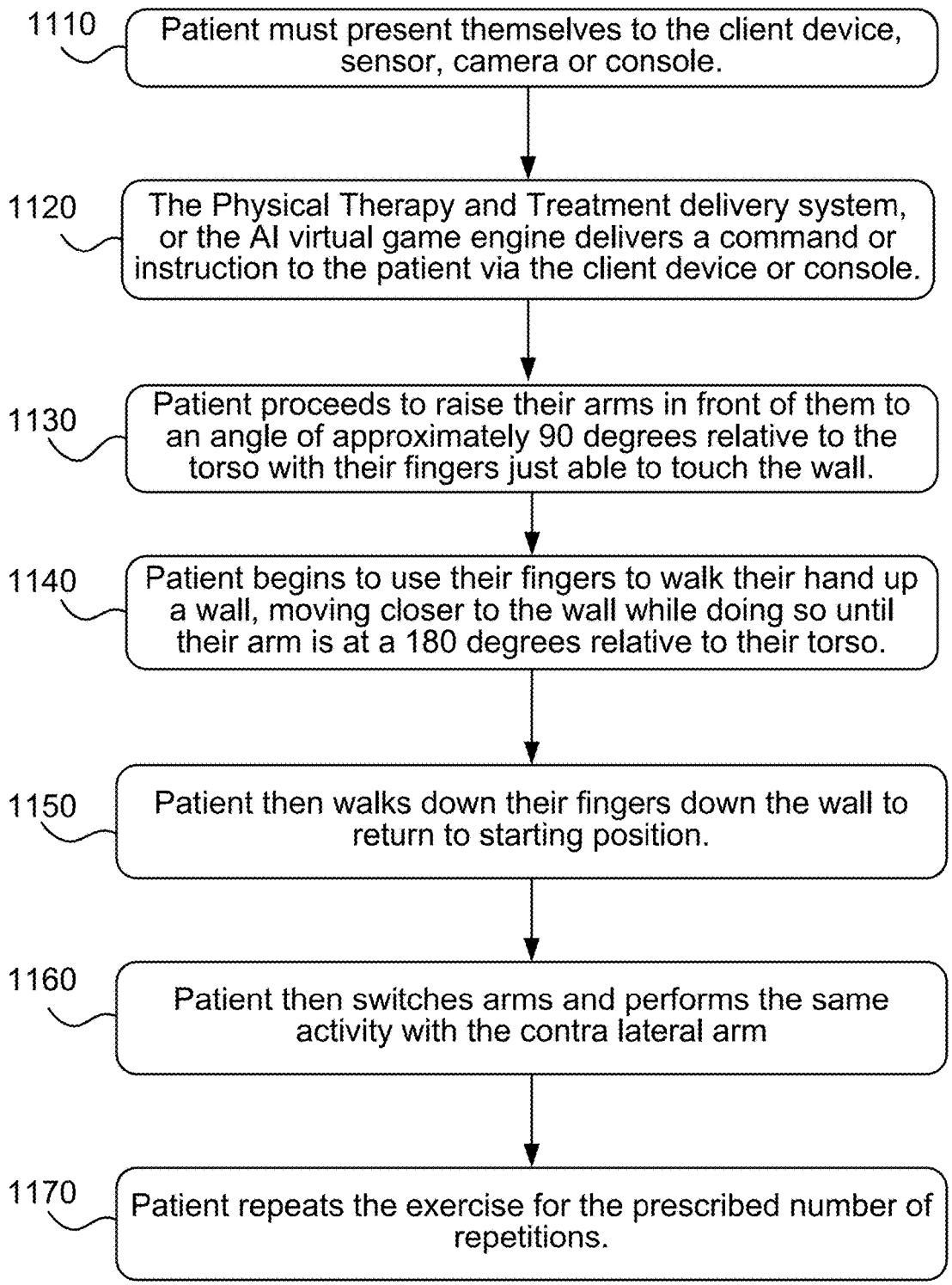

FIG. 11A presents one embodiment of an exemplary wall walking rehabilitation protocol.

Figure 11B:
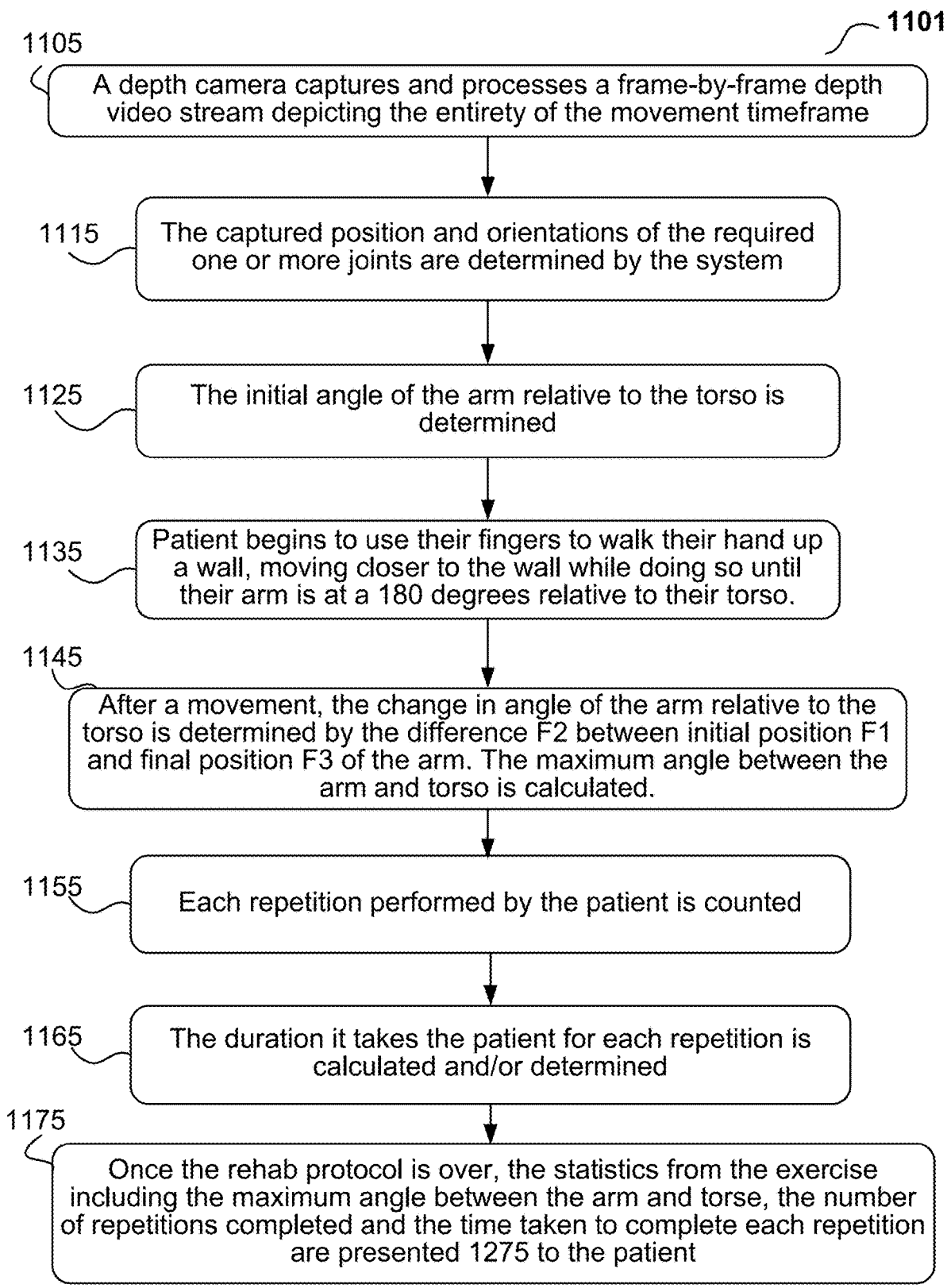

FIG. 11B presents one embodiment of the calculations carried out by the PTTD system and/or the AI game engine for a wall walking rehabilitation protocol.

Figure 12:
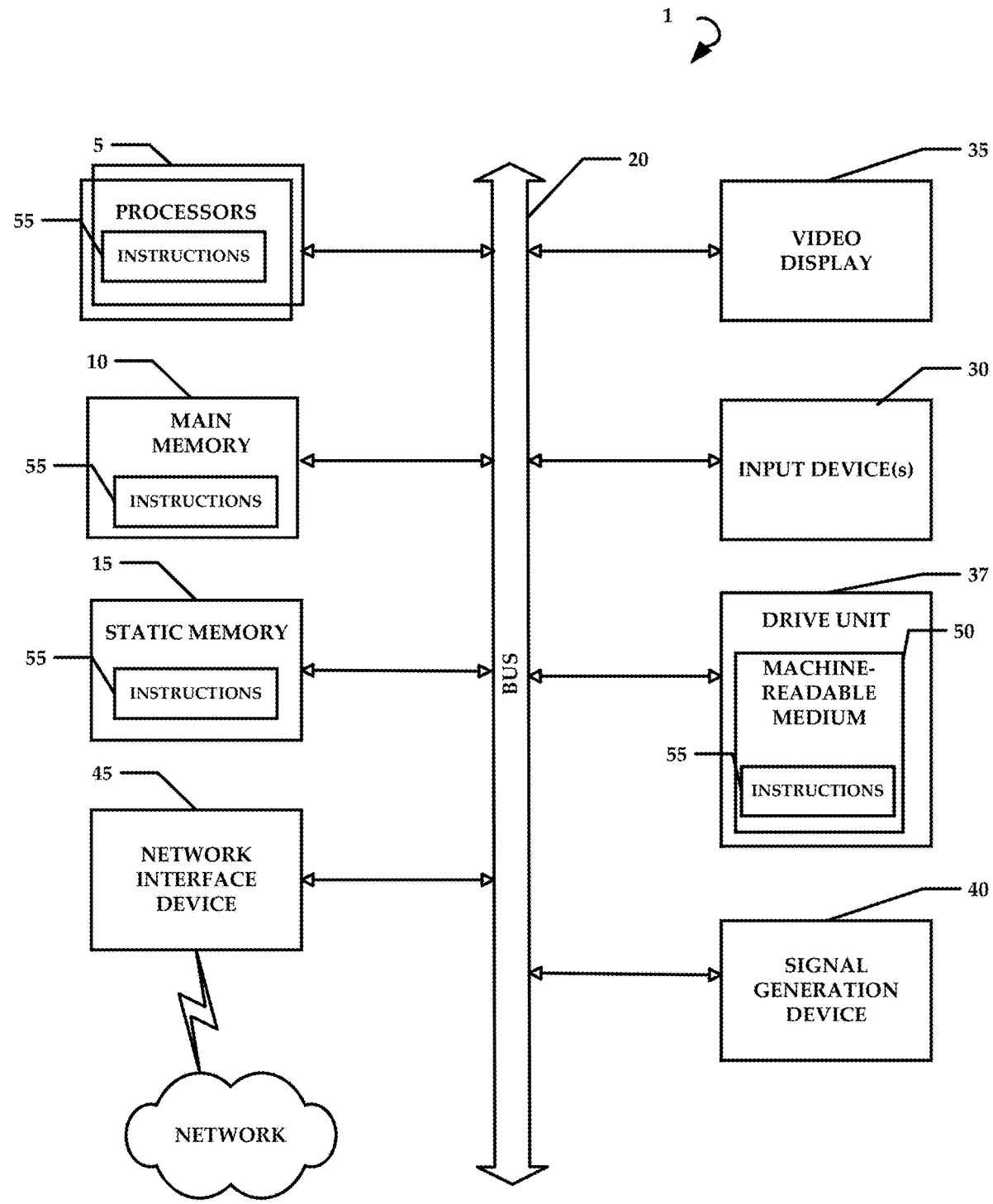

FIG. 12 illustrates a computer system according to exemplary embodiments of the present technology.

DETAILED DESCRIPTION

Physical therapy is provided as a primary care treatment or in conjunction with other forms of medical services. It is directed to addressing illnesses, injuries and trauma that affect an individual's ability to move or perform functional tasks. It can be an important component of many treatment regimens and is utilized in the treatment and long-term management of chronic conditions, illnesses and even the effects of ageing. It is also widely used in the treatment and rehabilitation of injuries, short-term pain and physical trauma.

Physical therapy may be composed of a number of components including the monitoring and/or assessment of patients, prescribing and/or carrying out physical routines or movements, instructing patients to perform specific actions, movements or activities, and scheduling short or long-term physical routines for patients; all these components designed to rehabilitate and treat pain, injury or the ability to move and perform functional tasks. Physical therapy may also contain an educational component directed to the patient and the patient's care circle.

Embodiments of the present technology provides systems and methods that enable physical therapy in some or all of its different forms to be undertaken and carried out remotely, from different locations and without any physical therapist or other individual being present with the patient.

While the present technology is susceptible of embodiment in many different forms, there is shown in the drawings and will herein be described in detail several specific embodiments with the understanding that the present disclosure is to be considered as an exemplification of the principles of the present technology and is not intended to limit the technology to the embodiments illustrated.

By making physical therapy remotely available to patients, the present technology enables a wide range of applications capable of addressing unmet needs in the areas of medical diagnostics, patient education, treatment, rehabilitation, communication and information sharing, and the like. There is generally a common need to find more cost-effective and scalable methods of assessing, monitoring and treating patients based on their medical history, future and long-term prospects, and their current physical status and abilities, as well as a need to deliver physical therapy in an accessible and standardized format to all patients, and in a variety of locations, with or without physical therapists or other individuals being physically present with the patient.

The term 'patient' is used to describe any individual that is using or intending to use or is prescribed the use of any embodiment of the systems and methods described herein, it may be used synonymously with the term 'user'. The term 'care circle' is used to describe individuals, organizations or entities that may be assigned either by the patient or by other means to be notified and informed of the patient's status, progress or need for immediate attention and/or help.

The remote physical therapy system provides and can incorporate and utilize different forms of motion detection, monitoring and tracking capabilities, in conjunction with analysis that may be executed and provided by artificial intelligence (AI) to both enhance the capture of audio-visual and other motion data as well as to provide analysis of the captured motion detection data and other available data. The AI engine may utilize amongst other factors, performance metrics from a patient carrying out physical therapy routines, or patient movement measurements, as variables to determine or calculate performance factors and metrics, patient health status, or other indicators of the patient's physical or mental state or wellbeing (all these collectively referred to as "patient state"). This system may also be able to integrate with, and read and/or write data to, electronic medical record systems of patients, and incorporate or utilize these records in analysis and other computations. A patient's historical data, both captured by the system and from external records, may serve as a baseline from which the system and AI engine uses to determine past, current, and future performance metrics or to provide insights into the health status of a patient. The assessment and analysis may also be carried out by analyzing metrics of performance, recovery, and fitness. The use of an AI engine is not strictly necessary.

Some embodiments of the system deliver routines to the patient's client device and display it with a graphical user interface, which may be that of an interactive avatar. The client device may be an Addison powered Artificial Intelligence based gait and physical therapy console, or a display device such as a cellular phone, tablet, computing device, and/or augmented reality or virtual reality headset/device or other audiovisual technology device. The interactive avatar may be able to perform routines or movements and provide instructions, feedback, information, communication, engagement or perform examples of physical therapy movements or routines for the patient or their care circle.

Some embodiments of the system may also be incorporated into smart home technologies, homecare, or other software applications or electronic devices that may assist in monitoring, observing, and ensuring compliance, or otherwise assist in detecting movement, measuring performance of patients, or even displaying the graphical user interface and/or interactive avatar. One or more plug-and-play input and output devices may also be used and be incorporated into the system.

Motion capture, skeletal tracking, detection of sounds, or the capture of infrared data may be undertaken by components embedded within a dedicated console or by plug-and-play or other devices that can be added to the system as desired, these devices may include microphones, cameras, including depth of field, infrared or thermal cameras, or other motion or image capture devices and technology. Some embodiments may incorporate air handling, air correction, skeletal tracking software and other detection and monitoring technologies.

Embodiments of the system may be able to detect movement, general health status and indicators, adverse reactions to drugs, sudden or rapid movements including but not limited to seizures, falls or heart attacks, or other changes in the physical or mental state of the patient based on visual, motion detection, skeletal tracking, sound, or other forms of captured data. It may detect or determine the patient state based on long or short-term analysis and/or calculations in conjunction with motion detection and/or analysis of a patient. It may also detect and/or determine the patient's state from data not directly collected or obtained from the physical therapy monitoring and assessment system. For example, data from the patient's records, medical history and of drug use may all be used.

In some embodiments, the system may be able to detect specific illnesses, diseases, deformities, or ailments suffered by the patient. One example could be detecting a parkinsonian shuffle from the gait velocity, time-in swing, time in double support, cadence, inverted pendulum measurement, or festination of a patient.

In various embodiments a notification or form of communication is sent to the patient's care circle, to notify them of changes in the patient state, non-compliance with scheduled routines or when certain movement(s) are detected. The form of notification or communication may be set or may be designated by the system depending on the severity of the detected motion or status of the patient. Notification may be carried out using any form of communication including but not limited to digital, electronic, cellular, or even voice or visual, and may be delivered through a monitor, television, electronic device, or any other interface that is able to communicate with or notify the patient or their care circle.

In various embodiments, the system may be deployed in hospitals, medical offices and other types of clinics or nursing homes, enabling on-site and live motion detection and analysis of patients. One example may be the detection of a patient that walks into a hospital, where the characteristics and datapoints collected from the patient's motion inside the premises are captured and analyzed, and a report is produced and transmitted/communicated to the designated physician. The physician seeing the patient will have up-to-date information prior to the visit that will inform the physician to look for certain symptoms, or possible health issues that were detected or red-flagged from the analysis of the patient's motion and/or other captured characteristics. This enables the physician to undertake tests or ask more detailed questions based on the indicators and report provided by the system.

In some embodiments, the system may prescribe specific movements or physical therapy routines, from a library containing a catalogue of physical therapy movements, routines, and regimens, to treat or rehabilitate patients or reduce their pain from injuries, to reduce future health risks, falls risk and other physical problems or potential for injuries. This library may be stored in a database accessible by users and other stakeholders. The prescribed movements and/or routines may be personalized for each person based on both captured personal data as well as the patient's external medical records or data. Artificial intelligence may be utilized to prescribe or provision specific movements, routines, or regimens. Artificial intelligence or machine learning may be used to detect and assess the patient's or user's health status, general health indicators and patient state, and prescribe and alter movements, routines and/or physical therapy plans accordingly. Artificial Intelligence may also access databases or other external information repositories and incorporate that data when tailoring, customizing, and provisioning movements, routines or plans according to the patient's goals or needs.

In some embodiments artificial intelligence uses the total information captured from all patients to devise new physical therapy movements, routines or plans it assesses to be beneficial to a specific patient, these movements or routines may be created and then added to a library containing a catalogue of physical therapy routines or movements. Devising new routines or movements allows for specific and more precise treatment plans to be delivered to each patient. These treatment plans may then be collected or organized into standardized plans that are delivered to other patients that possess certain common factors or indicators. Prescribed changes may then be sent to the patient's care circle.

A library containing all movements and routines/regimens may be updated by adding new routines or movements and may be accessed to update individual patient routines. Each movement, or routine comes with its own preset and calculated assessment metrics, performance variables, as well as associated notifications and instructions.

Physical Therapy Training and Delivery

Part 1. Individualized Provisioning

Various embodiments of the invention utilize an artificial intelligence virtual physical therapy exergame, physical therapy training and delivery (PTTD). PTTD delivers an exercise regimen or routine through a GUI. The exercise regimen can be individually tailored to improve a user's health status or condition by providing a customized approach to provisioning the virtual exercise programs. Provisioning of the user's regimen can be done by the individual or a qualified third party. A qualified third party can be, but is not restricted to, a user's physician, caregiver, or any other responsible party or member of the care circle. Provisioning of the regimen or routine includes, but is not restricted to, the selection of exercise(s), the number of sets, the number of repetitions, and the regimen schedule. The user may choose their programmed exercises from a non-relational database that connects to the GUI. The objects in the database serve as inputs to a schema that is programmed by the individual or third party. The schema pulls appropriate animations of the virtual caregiver to the user interface based on provisioned user inputs. Once a regimen is selected or added to the user's goals, the regimen is stored to the user's profile. The objective of PTTD is to improve patient mobility in a clinical aspect, however it is not limited to healthcare-based settings or outcomes for patients with ailments. For instance, PTTD can also be used in a cross-training environment to improve athletic performance of individuals and/or athletes.

Part 2. Clinical Development of Exercise Directory

Part 2.1 Exercise Directory

Physical therapists (PT) collaborate with PTTD developers to continually build and improve upon an exercise directory and animation motion capture footage. A licensed PT provides developers with accredited preventative and rehabilitative exercises for virtual instruction. The exercises are stored to a database for users' individualized provisioning. Each exercise in the database can be based on, but is not restricted to, anatomical or injury classification (e.g., hip strengthening or rib fracture rehabilitation.)

Part 2.2. Motion Capture with Licensed Physical Therapist

The database couples each exercise with its appropriate virtual caregiver animation. This animation serves as the set of exergame instructions for the user to follow. The avatar leads individuals through exercise. The motion capture (mocap) process for the animation is done utilizing mocap software. A developer in a mocap suit is recorded by cameras while performing exercises provided by the licensed PT. The PT supervises the developer through the motion capture process. The motion capture footage serves as the skeletal blueprint onto which the virtual caregiver's animation can be rendered. This ensures that the virtual caregiver instructs the patient with proper clinical form and modifications.

Part 3. Joint Tracking and Motion Analysis Integration

Part 3.1 Joint Tracking and Motion Analysis Via Depth Camera

PTTD records and measures a user's compliance with their provisioned regimen or routine. This is accomplished by joint tracking and motion analysis software that is integrated with a depth camera. The user's movements are recorded via a non-invasive depth tracking software that collects real-time spatial location of joints across a three-dimensional axis. Changes in the spatial location are calculated into a multitude of variables such as, but not limited to, the number of repetitions, cadence, gait velocity, stride length, range of motion, and time to completion. Prior to beginning the regimen, the user will go through a calibration routine that collects the user's anatomical ground-truth data. This allows the motion analysis software to track the user's movements with greater precision and accuracy. The user's ground-truth data is processed through the motion analysis software and labeled appropriately for future analysis. The user is prompted according to the provisioned regime to begin the prescribed activity. The user begins the activity, and their movements are recorded simultaneously as the provisioned regimen streams. All footage of users is made non-identifiable through a gray scale filter.

Part 3.2 Joint-Tracking with Analytics and Streaming Access

Each activity stream that is recorded by the depth camera gets appended on to the user's profile in a non-relational database. Each time a new activity stream is stored to the user profile, a machine learning algorithm (MLA) is triggered for analysis on joint-tracking data. The MLA compiles the user's calibrated ground truth data as a baseline to compare future joint-tracking data. The MLA can be, but is not limited to, supervised or unsupervised models that interpret when the user's kinesthetics are anomalous to their usual patterns. Anomalies detected by the MLA are classified as improvements or declines that are visualized on a GUI. Another option for additional insight is access to the user's stored activity data without MLA analysis. Upon user authorization, stored activity data can be available for playback. This allows the user or an authorized third-party to review streaming footage to validate compliance and kinesthetic progress at their own discretion and provides another source of ground-truth for the models.

Part 4 Data Storage 4.1 Individual Database

Another valuable component of PTTD is the cloud-based data store. Gait and posture are unique to an individual based on personal characteristics and features such as medical history, age, and gender. One impediment in machine-learning based motion analysis is obtaining ground-truth data. What could be interpreted as anomalous movement for one user could be classified as an improvement for another if compared to a general population average. To address this, PTTD implements two methods of analysis: an individualized model, and a population-based model. Each time motion analysis is triggered for an individual, the data is stored to their user database. The individualized model has a user database that restricts its analysis to ground-truth data supplied only by the individual. The progress reports from the individual's database are compared to their personal ground-truth data set. As the user increases their PTTD usage, the motion analysis tailors insights to their individual baselines with the new datapoints, and this additional data allows the algorithm to gain additional insight into developments or progress in the user's kinesthetics. This allows the motion analysis algorithm to continually retrain itself for improved accuracy.

4.2 Population Data Lake

From these individual databases, data is pulled into a general population data lake to provide further macro-scale or big data insights. Authorization to access the data lake can be granted to any individual organization through an ordering process. This makes ground-truth data available to those who do not have access to the physical hardware and the infrastructure that goes into collection of motion analysis data but wish to perform research and development using the data lake's features. All data is encrypted at rest and in transit.

FIG. 1 illustrates an exemplary generalized architecture for practicing some embodiments of the remote physical therapy system.

The remote physical therapy system 100 includes a sensor 111 enabled to capture data, a client device 110 that displays an interactive avatar through a graphical user interface 112, a server system 105 that includes an AI Virtual Game Engine 120 which provides the functionality of the system and all of its embodiments as described throughout this document. The system may also include an Electronic Medical Record system 125. The different components of the system are connected via a network 115.

FIG. 2 illustrates an exemplary architecture for practicing aspects of the present technology that provides a more detailed view of aspects of the system. The architecture comprises a server system, hereinafter "system 205" that is configured to provide various functionalities, which are described in greater detail throughout this document. Generally, the system 205 is configured to communicate with client devices, such as client 210. An example of a computing device that can be utilized in accordance with the present technology is described in greater detail with respect to FIG. 13.

The system 205 may communicatively couple with the client 210 via a public or private network, such as network 215. Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 215 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital, or analog interface or connection, mesh or Digi® networking.

The system 205 generally comprises a processor, 230, a network interface 235, and a memory 240. According to some embodiments, the memory 240 comprises logic (e.g., instructions) 245 that can be executed by the processor 230 to perform various methods. For example, the logic may include a user interface module 225 as well as an AI virtual Game Engine 220 which includes data aggregation and correlation (hereinafter application 220) that is configured to provide the functionalities described in greater detail herein including systems and methods of remote physical therapy.

It will be understood that the functionalities described herein, which are attributed to the system 205 and application 220 may also be executed within the client 210. That is, the client 210 may be programmed to execute the functionalities described herein. In other instances, the system 205 and client 210 may cooperate to provide the functionalities described herein, such that the client 210 is provided with a client-side application that interacts with the system 205 such that the system 205 and client 210 operate in a client/server relationship. In some embodiments, complex computational features may be executed by the system 205, while simple operations that require fewer computational resources may be executed by the client 210, such as data gathering and data display.

FIG. 3 is a diagrammatical representation that illustrates the basic flow of a user profile set 300 in the PTTD system. The user logs in to PTTD and is presented with a Start screen 305 with the option to either provision 310 or begin 330 an exercise regimen. Exercise regimens can be triggered manually by the user or through a reminder. All user activity data is stored to their user profile. Provisioning 310 will allow the user to create a new (or modify an existing set 312) individualized exercise or physical therapy rehabilitation set. Provisioned exercise regimens can also be tailored by an individual or third-party (such as the patient's care circle). The patient must be verified 320 first by the system, through image, voice or other biometric identification known in the art. Once the user's identity is verified or confirmed 320, the patient may access the User Profile screen 325 that contains information and data, including but not limited to historical progress reports, joint-tracking motion analysis results, exercise regimen(s), diet information, medical and health records, prescribed medications, as well as supplementation and other health related activities or logs that the patient has been keeping or that has been kept for the patient by a computing device, care circle, physician, therapist or smart IoT and/or tracking technologies. In various embodiments the Start screen 305 instantly takes a user to a User Profile screen 325. The provisioned program from step 310 may also be stored 315 into the user profiles. When a user starts or chooses to begin 330 an exercise regime, the activity begins 340, in one embodiment an avatar demonstrates to, or leads the user through exercise or rehabilitative movements and therapy. As the user undertakes the activity, the PTTD system collects Joint-tracking and motion-analysis information 350. In various embodiments when the data is collected it is also analyzed in this step, locally, via a network, on a server, or on a cloud server system. Once the user ends activity 360, whether completed or not, the data collected is stored to the user profile, user tables, databases, or all these.

FIG. 4 illustrates the Run Motion Analysis Interface 400. This is the initial interface to run motion analysis assessment in either Clinical or Validation modes. Motion analysis assessment usually comprises 3 steps, setting up the test, performing the test and viewing results. Clinical mode is for performing the specified assessment to measure patient progress. Validation mode is available to clinicians who wish to review user data. In some embodiments a button or slider 410 may be toggled to switch between Validation and Clinical modes. The user may also have the option to select the type of test 420.

FIG. 5 illustrates the motion analysis joint-tracking interface 500. The joint-tracking assessment 510 measures the changes in the position of the pelvis, neck, and head, and these are plotted against time to measure number of repetitions, velocity, and time to completion.

FIG. 6 illustrates a Validation Mode User Profile Activity Access interface 600. This is an interface that allows clinicians to review multiple users'/patients' results. A user of the interface or clinician may select the test 610 that the data is sought for. The user's ground-truth data are processed through the motion analysis software and labeled appropriately for future analysis. The data may be presented in analysis tables 620 and 630.

Figure 7C:
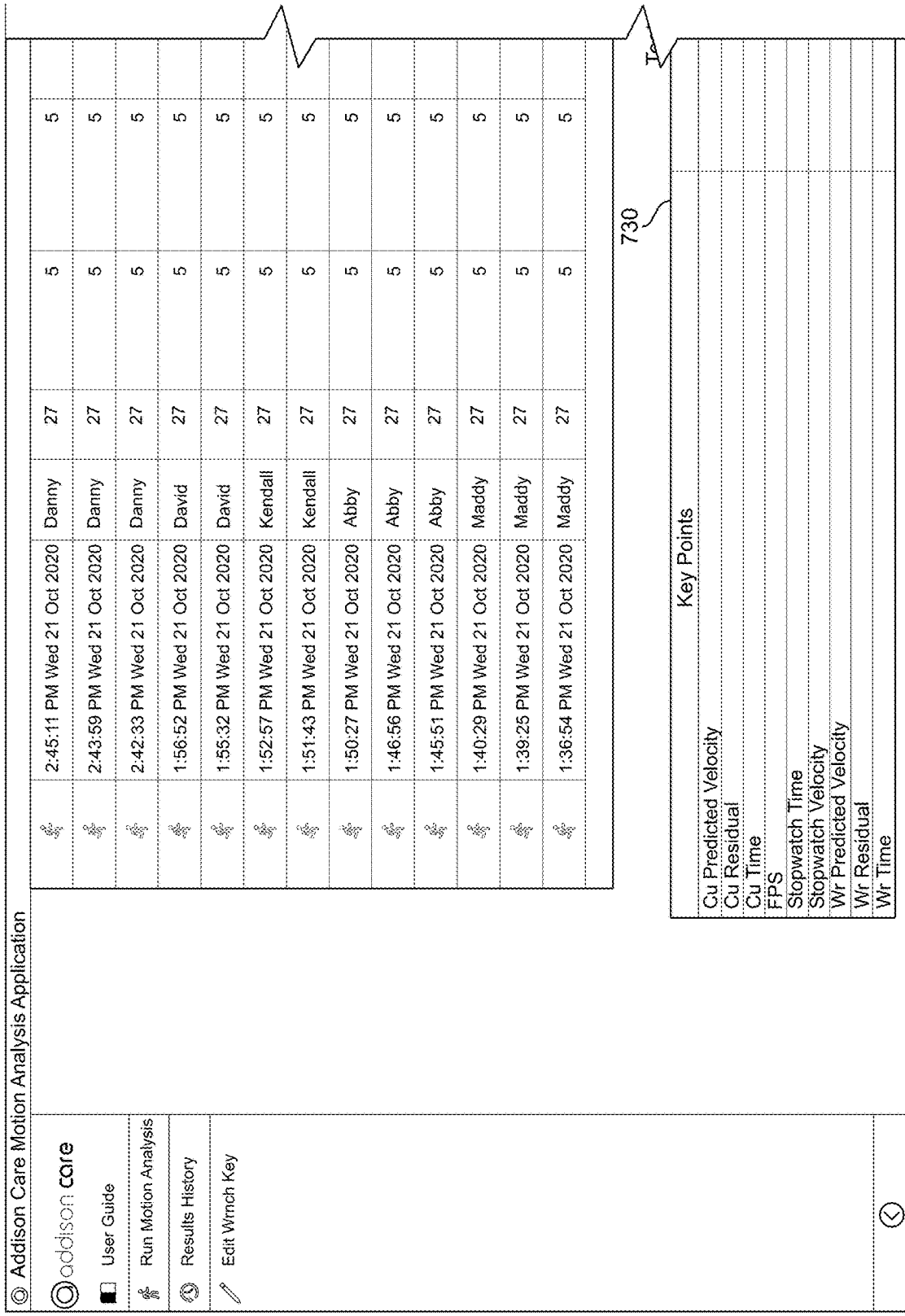
Figure 7D:
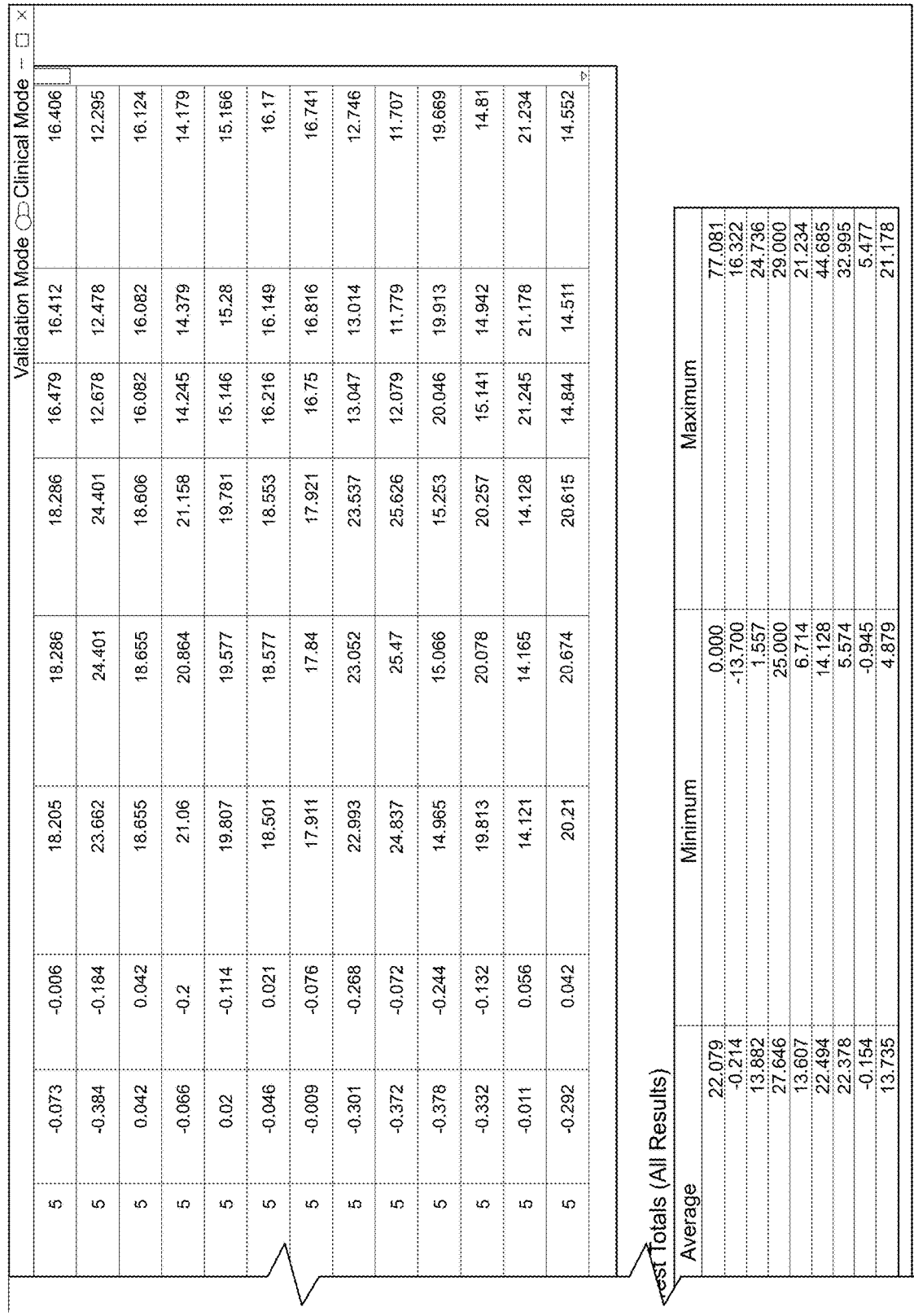

FIGS. 7A-7D illustrate the interface for multi-user ground truth comparison 700. This is a ground-truth comparison interface that allow clinicians to compare user results 710 of one or multiple users for further insight and analysis, and for each test 720 undertaken. In several embodiments, an MLA compiles the users' calibrated ground truth data as a baseline to compare future joint-tracking data. FIGS. 7A and 7B show the top half of the interface screen, while FIGS. 7C and 7D show the bottom half of the interface screen. A Test Totals table 730 showing all results collected, presents derived and analyzed data from all tests run.

FIG. 8 presents flow diagram of a method 800 to capture and process depth image and scene data as part of the PTTD system. In several embodiments a motion capture module is deployed along with a depth camera. In some embodiments the motion capture module may be contained in, be part of, or connected to an AI virtual game engine. The depth camera may calculate depth in various ways including and not limited to stereo vision technology. Stereo vision technology is utilized by having the depth camera capture 805 left and right image(s) of a particular object or movement. The captured scenes and scene data are transmitted 810 (for example in pixels) to an internal or external depth image processor. The image processor then calculates 815 the depth of each pixel. The depth values of each pixel are then processed by an imager to create a depth frame 820. The combination of multiple depth frames create a depth video stream 825. Specially designed software then applies 830 a point cloud over the depth video stream, which allows for estimates of position and orientation of body joint centers to be calculated 835 across the entirety of the depth stream. Finally, position and orientation estimates are then processed 840 using accepted calculations known in the art.

FIG. 9A presents a diagram for a method 900 for Physical therapy and training delivered by an exemplary AI virtual game engine. In some embodiments, the AI game engine may be stored, run, or executed on a server. In other embodiments the AI game engine may be stored, run, or executed on a serverless, or cloud-based systems, or alternatively on a client, console or computing device, or a combination of all of these. In several embodiment the AI game engine ("AI") executes the PTTD by scheduling one or more physical therapy activities for a patient and provide reminders for exercises to be performed by the patient.

The AI game engine creates or is given a physical therapy schedule for a patient 910. The AI game engine sends a reminder to the patient or the patient's client device or console 920. The client device or console delivers the reminder or notification to the patient 930. If the patient does not acknowledge the reminder, the patient's care circle is notified 935. Otherwise, the patient acknowledges the reminder 940. In some embodiments, the patient may have to confirm their identity 945 to the client device or console. Only after confirmation of the patient's identity does the client device or console receive and/or display the patient's routines or other private data. The console or client device may confirm the identity of the patient via facial recognition or via other biometric means. If the patient chooses not to perform the physical therapy activity, an alert is generated, and the patient's care circle is notified 950. Otherwise, the patient chooses, accepts, or confirms that the activity will be performed to the client device or console 955. The movements are demonstrated 960 to the patient via the client device or console, in many embodiments with an avatar. The patient then indicates that he/she is ready to begin demonstrated activity 965. The client device or console requests that the patient move into a correct position or orientation relative to the client device, console, or camera 970.

FIG. 9B continues from FIG. 9A where a depth camera collects footage of the patient performing the activity 980. Depth footage is processed 990 locally on the client device or console to identify quantitative markers of the activity. One way the depth camera may process 990 the image data is via the method presented in FIG. 8. Data is transmitted to the server or other backend system 995. Captured patient data which may be comprised of captured image, frame, video, performance, biometric or any other patient data may be further processed by the backend system, server, or AI virtual game engine 997. Processed data is then displayed and presented 998 to the patient via the client device or console. The data can be depicted in tabular or graphical form for analysis of trends or changes in patient movements, or another relevant patient score.

FIG. 10A presents one possible embodiment of a functional reach testing protocol 1000 carried out by the PTTD system for patients. In this embodiment, to perform a functional test, for example a reach test, the patient must present themselves 1010 in front of the console or client device and/or the depth camera, for example by standing in front of the camera, making sure that one or more of the following required joints are visible to the depth camera, right heel, left heel, right hip, left hip, right wrist, left wrist, torso, neck and head. Of course, the joints that must be visible to the camera depend on the requirements of each test. Each test may require one, some, or all the joints to be visible. The PTTD system delivers a command or instruction 1020 to the user, which may be a voice instruction, the patient raises either left or right arm and proceeds to reach in front of them as far as they can 1030. Patient continues to reach 1040 until they are required to either raise their heels from the ground or change the hip/torso angle. Patient then returns to starting position 1050, optionally repeating the process for the other side.

FIG. 10B presents one possible embodiment of the calculations carried out 1001 by the PTTD system and/or the AI game engine for the functional reach test discussed in FIG. 10A. The depth camera captures the scenes of the patient performing the test or activity and combines them into a frame-by-frame depth stream 1005. One way this may be undertaken is presented in more detail in FIG. 8. The positions, orientations, displacement, and movement of the required one or more joints are determined 1015 by the system. These joints may include any one or more of, and not limited to: the right heel, left heel, right hip, left hip, right wrist, left wrist, torso, neck and head. The horizontal linear displacement of the wrist joint from point F1 to point F3 is calculated 1025 by the difference F2 between the two points F1 and F3 (i.e., F3−F1=F2). The delta angle of the torso relative to the hip is calculated 1035. The delta or change 1045 in the angle of the torso relative to the hip from point F1 to point F3 is calculated. The vertical position of the heels is determined 1055. The vertical change in position of the heel is then calculated 1065 by the difference between initial point F1 and final point F3 and the difference F2 between the two points (F3−F1=F2). In various embodiments the horizontal axis linear distance reached by the patient is delivered or presented 1075 to the patient through a console or client device.

FIG. 11A presents one embodiment of an exemplary rehabilitation protocol 1100, wall walking. The patient must present themselves 1110 in front of the console or client device and/or the depth camera, for example by standing in front of the camera, making sure that one or more of the following joints are visible to the depth camera, right heel, left heel, right hip, left hip, right wrist, left wrist, torso, neck, and head. Of course, the joints that must be visible to the camera depend on the requirements of each test. In this test the patient stands near a wall within their environment visible to the depth camera. Each test may require one, some, or all, of the joints to be visible. The PTTD system delivers a command or instruction 1120 to the user, which may be a voice instruction, the patient then raises their arms 1130 in front of them to an angle of approximately 90 degrees relative to the torso with their fingers just able to touch the wall. Patient then begins to use their fingers to walk their hand up the wall 1140, moving closer to the wall until their arm is at 180 degrees (or as high as possible) relative to the torso. Patient uses their fingers to then walk back down the wall and return to starting position 1150. Patient then switches arms and performs the same activity with the contra lateral arm 1160. Repeat for the prescribed number of repetitions for each arm 1170.

FIG. 11B presents one possible embodiment of the calculations carried out 1101 by the PTTD system and/or the AI game engine for the functional reach test wall walking rehabilitation protocol discussed in FIG. 11A. The depth camera captures and processes 1105 a frame-by-frame depth video stream depicting the entirety of the movement timeframe. One way this could be carried out is by the process as described in FIG. 8. The captured position and orientations of the required one or more joints are determined 1115 by the system. These joints may include any one or more of, and not limited to: the right heel, left heel, right hip, left hip, right wrist, left wrist, torso, neck and head. The initial angle of the arm relative to the torso is determined 1125. After a movement, the change in angle of the arm relative to the torso is determined 1135, by the difference F2 between initial position F1 and final position F3. The maximum angle between the arm and torso is calculated 1145. Each repetition performed by the patient is counted 1155. The duration it takes a patient for each repetition is also determined 1165. Once the rehab protocol is over, the statistics from the exercise including the maximum angle between the arm and torse, the number of repetitions completed, and the time taken to complete each repetition are presented 1175 to the patient.

FIG. 12 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network (e.g., network 115, see FIG. 1 or network 215, see FIG. 2) via the network interface device 45 utilizing any one of several well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that can store, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized to implement any of the embodiments of the disclosure as described herein.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel or may be performed at different times.

While various embodiments have been described above, they are presented as examples only, and not as a limitation. The descriptions are not intended to limit the scope of the present technology to the forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed is:

1. A method for remote physical therapy and assessment, the method executed by at least one processor, comprising:
   capturing, via one or more sensors, frames of a patient undertaking a prescribed activity;
   processing the captured frames of the patient undertaking the prescribed activity;
   the capturing of the frames being undertaken by a left sensor and a right sensor; and
   the processing of the captured frames comprising:
      transmitting the captured frames to an internal depth image processor, wherein the captured frames consist of pixel data of one or more captured scenes;
      calculating, by the internal depth image processor, a depth of each pixel, to produce depth pixel values;

processing, by the internal depth image processor, the depth pixel values to create a depth frame;

combining, by the internal depth image processor, the depth frames into a depth video stream;

applying a point cloud over the depth video stream; and estimating position and orientation of the patient's body joint centers.

2. The method of claim 1, wherein the captured frames are depth scene frames.

3. The method of claim 1, wherein the one or more sensors are cameras, imagers, image capture devices, or depth cameras.

4. The method of claim 1, wherein the processing occurs on a client device or console.

5. The method of claim 1, further comprising:
instructing the patient to get into a specific position or orientation.

6. The method of claim 1, further comprising:
transmitting results of the processing of the captured frames to an AI game engine or a backend system, wherein the AI game engine or the backend system can analyze trends or changes in a movement of the patient; and
presenting the analyzed results to the patient via a graphical user interface on a client device or console.

7. The method of claim 1, wherein failure to confirm patient's acknowledgment, or that the patient is undertaking or will be undertaking the prescribed activity, causes a notification to be sent to a care circle.

8. A system for remote therapy and assessment of patients, comprising:
an AI virtual game engine, to analyze captured frame data and produce updated personalized instructions;
the capturing of the frames being undertaken by a left sensor and a right sensor; and
the processing of the captured frames comprising:
transmitting the captured frames to an internal depth image processor, wherein the captured frames consist of pixel data of one or more captured scenes;
calculating, by the internal depth image processor, a depth of each pixel, to produce depth pixel values;
processing, by the internal depth image processor, the depth pixel values to create a depth frame;
combining, by the internal depth image processor, the depth frames into a depth video stream;
applying a point cloud over the depth video stream; and
estimating position and orientation of the patient's body joint centers.

9. The system of claim 8, further comprising:
a network, whereby the network is connected to at least one of the sensors, at least one on-location client device or console, and the AI virtual game engine.

10. The system of claim 8, wherein the captured frames are depth scene frames.

11. The system of claim 8, wherein the sensors are cameras, imagers, image capture devices, or depth cameras.

12. The system of claim 8, wherein the processing occurs on a client device or console.

13. The system of claim 8, further comprising:
instructing the patient to get into a specific position or orientation.

14. The system of claim 8, further comprising:
transmitting results of the processing of the captured frames to the AI virtual game engine or a backend system, wherein the AI virtual game engine or the backend system can analyze trends or changes in a movement of the patient; and
presenting the analyzed results to the patient via a graphical user interface on a at least one client device or console.

15. The system of claim 8, wherein failure to confirm patient's acknowledgment, or that the patient is undertaking or will be undertaking the prescribed activity, causes a notification or alert to be sent to a care circle.

16. The system of claim 8, further comprising:
instructing the patient to get into a specific position or orientation.

17. A non-transitory media having instructions for executing a method by a processor, the method comprising:
capturing, via one or more sensors, frames of a patient undertaking a prescribed activity; and
processing the captured frames of the patient undertaking the prescribed activity, wherein the processing comprises:
transmitting the captured frames to an internal depth image processor, wherein the captured frames consist of pixel data of one or more captured scenes;
calculating, by the internal depth image processor, a depth of each pixel, to produce depth pixel values;
processing, by the internal depth image processor, the depth pixel values to create a depth frame;
combining, by the internal depth image processor, the depth frames into a depth video stream;
applying a point cloud over the depth video stream; and
estimating position and orientation of the patient's body joint centers;
transmitting the results of the processing of the captured frames to an AI game engine or a backend system, wherein the AI game engine or the backend system can analyze trends or changes in a movement of the patient; and
presenting the analyzed data to the patient via a graphical user interface on at least one client device or console;
wherein the capturing of the frames is undertaken by a left sensor and a right sensor.

18. The non-transitory media having instructions for executing the method by the processor of claim 17, the method comprising:
notifying a patient of a scheduled prescribed activity via an on-location the at least one client device or console.

19. The non-transitory media having instructions for executing the method by the processor of claim 18, the method comprising:
identifying the patient with the one or more sensors connected to or part of the at least one client device or console.

20. The non-transitory media having instructions for executing the method by the processor of claim 19, the method comprising:
confirming, via the at least one client device or console, the patient's acknowledgment of a notification.

* * * * *